United States Patent
Ansell et al.

(10) Patent No.: US 8,486,924 B2
(45) Date of Patent: Jul. 16, 2013

(54) TAXANE DELIVERY SYSTEM

(75) Inventors: Steven M. Ansell, Princeton, NJ (US);
Sharon Johnstone, Princeton, NJ (US);
Paul Tardi, Princeton, NJ (US);
Lawrence Mayer, Princeton, NJ (US)

(73) Assignee: Celator Pharmaceuticals, Inc., Princeton, NJ (US)

( * ) Notice: Subject to any disclaimer, the term of this patent is extended or adjusted under 35 U.S.C. 154(b) by 271 days.

(21) Appl. No.: 12/741,954

(22) PCT Filed: Nov. 26, 2008

(86) PCT No.: PCT/US2008/085030
§ 371 (c)(1),
(2), (4) Date: Sep. 13, 2010

(87) PCT Pub. No.: WO2009/070761
PCT Pub. Date: Jun. 4, 2009

(65) Prior Publication Data
US 2010/0331290 A1    Dec. 30, 2010

Related U.S. Application Data

(60) Provisional application No. 60/990,907, filed on Nov. 28, 2007.

(51) Int. Cl.
*A61K 31/58* (2006.01)
*A61K 31/335* (2006.01)
*A61K 31/27* (2006.01)
*A61K 47/00* (2006.01)

(52) U.S. Cl.
USPC ............ 514/172; 514/449; 514/489; 514/785

(58) Field of Classification Search
USPC ................... 514/172, 449, 489, 785
See application file for complete search history.

(56) References Cited

U.S. PATENT DOCUMENTS

| 5,534,499 A * | 7/1996 | Ansell .............................. 514/25 |
| 6,291,690 B1 | 9/2001 | Mayhew et al. |
| 2003/0191179 A1 | 10/2003 | Joshi-Hangal et al. |
| 2008/0299205 A1 * | 12/2008 | Mayer et al. .................. 424/489 |

FOREIGN PATENT DOCUMENTS

| JP | 2004-285026 | 10/2004 |
| JP | 2007-509978 | 4/2007 |
| WO | WO-94/05282 | 3/1994 |
| WO | WO-03/028696 | 4/2003 |
| WO | WO-2005/042539 | 5/2005 |
| WO | WO-2006/014626 | 2/2006 |

OTHER PUBLICATIONS

Jiang et al. Am. J. Clin Nutr (2001); 74: 714-722.*
Glide et al. Electrochimica Acta 45 (2000) 3823-3831.*
International Search Report for PCT/US08/85030, mailed on Jan. 22, 2009, 2 pages.
International Preliminary Report on Patentability for PCT/US08/85030, issued Jun. 1, 2010, 5 pages.
Stevens et al., "A Folate Receptor-Targeted Lipid Nanoparticle Formulation for a Lipophilic Paclitaxel Prodrug", Pharmaceutical Research (2004) 21(12):2153-2157.
Supplementary European Search Report for EP 08855240.1, mailed Nov. 26, 2012.
Zhang et al., "Synthesis and characterization of the paclitaxel/MPEG-PLA block copolymer conjugate", Biomaterials (2005) 26:2121-2128.
Notice of grounds for rejection for JP 2010-536196, mailed Apr. 16, 2013.

* cited by examiner

*Primary Examiner* — Shirley V Gembeh
(74) *Attorney, Agent, or Firm* — Morrison & Foerster LLP

(57) ABSTRACT

Nanoparticulate formulations for delivery of taxane conjugate prodrug formed from a taxane coupled to a hydrophobic moiety through a glycolate linker are described.

16 Claims, 5 Drawing Sheets

Panel A: Elimination of 1 (○) and 2 (●) in prodrug/VES/2kPS3k (1:1:2; w/w) formulations labeled with $^3$H-CHE (□ and ■ respectively) in athymic nude $Foxn1^{nu}$ mice dosed at 35 mg drug/kg doses (n = 3/timepoint) Panel A. Drug concentrations were determined by HPLC analysis of plasma recovered at various time points. Panel B: Relative drug retention was determined using the ratio of drug/$^3$H CHE in individual mice for 1 and 2 systems (△ and ▲ respectively). Error bars represent standard deviation (n=3).

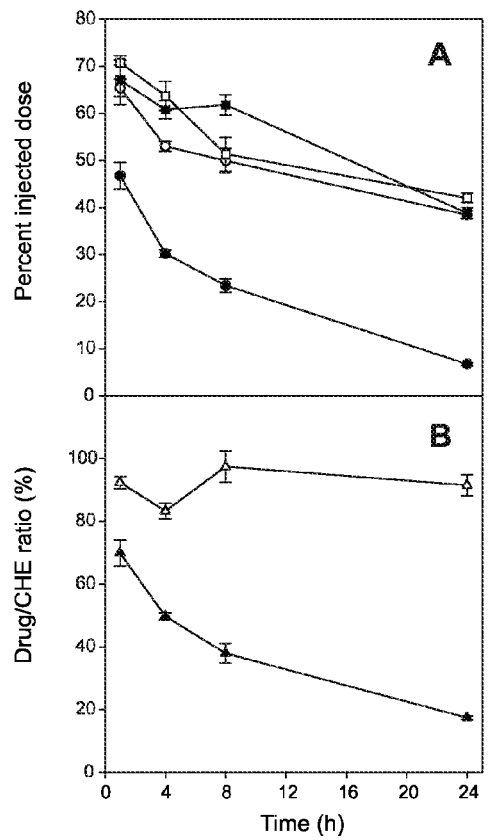

Figure 1

Elimination of prodrug formulated as prodrug/POPC/2kPS3k (1:1:2; w/w) formulations and administered intravenously to athymic nude $Foxn1^{nu}$ mice at a dose of 7 mg/kg (n = 3/timepoint). Drug concentrations were determined by HPLC analysis of plasma isolated at various time points. The prodrugs used were: 1 (●); 2 (○); 3 (◇); 4 (■); 5 (□); 6 (▲); 7 (△); 8 (▼); and 9 (▽). Error bars represent standard deviation (n=3).

Relative efficacy of prodrugs formulated as prodrug/POPC/2kPS3k (1:1:2; w/w) nanoparticles when administered to athymic nude mice bearing HT29 human colon carcinoma xenographs. Drug was administered at a dose of 36 μmol/kg using a Q4Dx6 schedule. The prodrugs and controls used were Saline (●), 1 (□), 2 (▲), 4 (▽), 5 (◆), 6 (○), 7 (■). Error bars represent standard deviation (n=6).

Effect of dose on the efficacy of 7/POPC/2kPS3k nanoparticles in the HT29 human colon carcinoma model. Athymic nude mice were injected intravenously with formulations 14 days after tumor cell inoculation. 7/POPC/2kPS3k (1:1:2) was administered at 69 μmol/kg (3X paclitaxel equivalents, □), 46 μmol/kg (2X paclitaxel equivalents, △), 34 μmol/kg (1.5X paclitaxel equivalents, ▽), 23 μmol/kg (1X paclitaxel equivalents, ◇) and 5.7 μmol/kg (0.25X paclitaxel equivalents, ▼) using a Q2Dx5 schedule. Saline (Q2Dx5, ■) was used as a negative control. Taxol® was administered at 23 μmol/kg using a Q2Dx5 (●) dosing schedule. Error bars represent standard deviation (n=6).

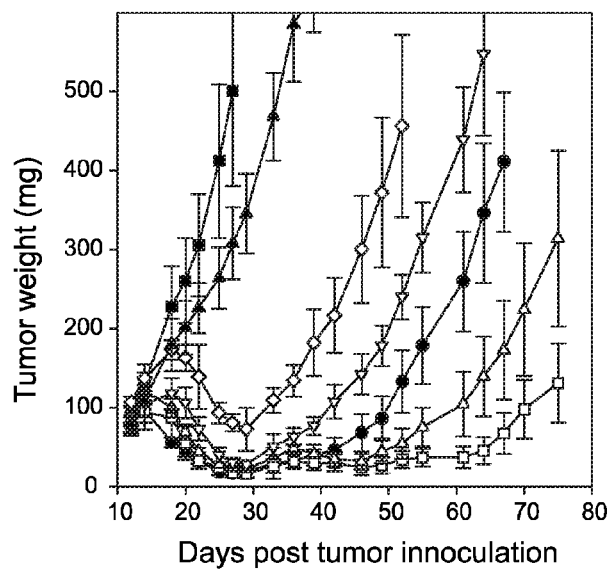

Figure 4

*Calculation of the number of paclitaxel equivalents of 7 required to reach parity with Taxol™.*

The tumor growth data was analyzed by two methods to determine what dose of 7 would be equivalent to the Taxol® positive control.

The delay in reaching a tumor size of 300 mg was measured relative the saline negative control and then normalized against the delay observed for the Taxol® group. Plotting the relative delay against paclitaxel dose equivalents of 7 yielded a linear dose response which showed that parity with the Taxol® group was achieved with 1.65 paclitaxel equivalents of 7.

The delay in reaching a tumor size of 125 mg was measured from the start of treatment and then normalized against the delay observed for the Taxol® group. The relative delay was plotted against paclitaxel dose equivalents of 7, yielding a data set that showed a linear dose response up to the MTD of 7. The fitted curve indicated that 7 achieved parity with Taxol® at a dose of 1.75 dose equivalents of paclitaxel.

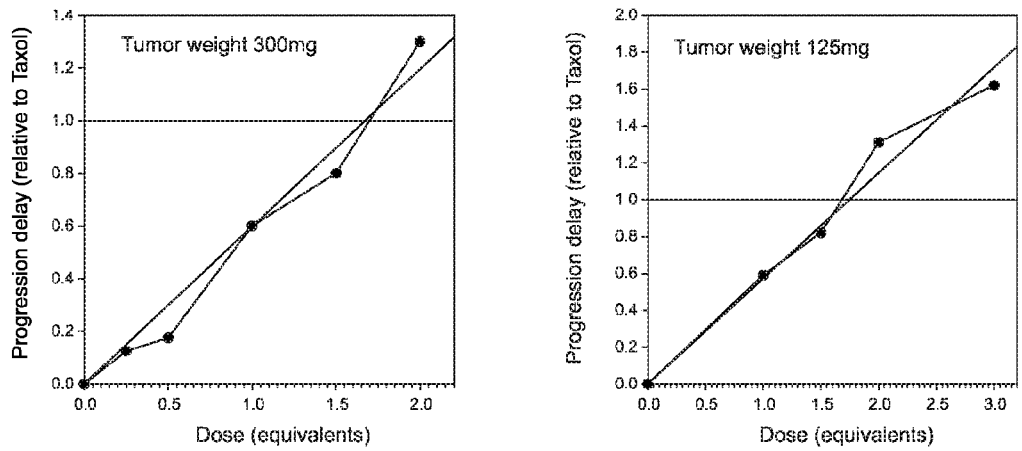

Figure 5

TAXANE DELIVERY SYSTEM

CROSS-REFERENCE TO RELATED APPLICATIONS

This application is the national phase of PCT application PCT/US2008/085030 having an international filing date of 26 Nov. 2008, which claims benefit of U.S. provisional application No. 60/990,907 filed 28 Nov. 2007. The contents of the above patent applications are incorporated by reference herein in their entirety.

RELATED APPLICATION

This application claims benefit of U.S. application Ser. No. 60/990,907 filed 28 Nov. 2007 which is incorporated herein by reference in its entirety.

TECHNICAL FIELD

The invention is in the field of drug delivery, specifically in the area of successful delivery of taxanes with controlled pharmacokinetics.

BACKGROUND ART

Paclitaxel is a widely used chemotherapeutic agent for treating a range of carcinomas. The clinical material is formulated in Cremophor® EL/ethanol, and is diluted with buffer prior to administration. There are many reports in the literature describing attempts to improve the formulation of paclitaxel using micelles, liposomes or emulsions.[1, 15, 16, 17] In almost all cases, however, it is clear from the reported pharmacokinetic data that while these carriers formulate paclitaxel, they do not act as true delivery vehicles in vivo since the drug rapidly partitions out of the carrier with half lives on the order of minutes. One exception appears to be a formulation known as NK105.[2] NK105 is paclitaxel formulated in micelles comprised of poly(ethyleneglycol)-poly(aspartic acid) in which the carboxyl groups are capped with 4-phenylbutanol.

Many attempts have also been made to produce functional lipophilic paclitaxel prodrugs to improve the performance of paclitaxel or to address formulations issues associated with the drug. These include conjugates with phospholipids[3, 4], cholesterol[5], α-bromo fatty acids[6, 7], oleic acid[8, 9], fullerene[10] and docosahexanoic acid[11]. These prodrugs were formulated in lipid vehicles, such as liposomes[3, 7, 10], oil emulsions[8, 9] or micelles[5, 6, 11]. In addition, WO2006/014626 discloses conjugates of paclitaxel and other drugs with hydrophobic moieties which may exist in particulate form. Most of these reports claim improved efficacy over paclitaxel in in vivo models, however, in most cases they either provide no information on plasma drug elimination or present data focusing on the terminal drug elimination phase rather than the early distribution phase. Drug elimination information during the first 24 h after administration is the period of most significant interest from a tumor delivery perspective due to the enhanced permeability and retention (EPR) phenomenon observed with particulate carriers, including micelles and nanoparticles.

The invention is exemplified by a series of lipophilic paclitaxel prodrugs and associated micellar/nanoparticle formulations. Particulate delivery vehicles with prolonged circulation half lives are described where the release of drug is modulated by manipulating the degree of a lipid anchor hydrophobicity and the lability of the prodrug cross-linkers. The efficacy of the prodrugs in vivo are shown to be dependant on the nature of the linkage and the relative partitioning rate of the lipid anchor.

Many chemotherapeutic treatment regimes involve multiple drugs. Many drug combinations act synergistically at appropriate ratios, but antagonistically at other ratios in cell based studies. When these findings are applied to in vivo studies different pharmacokinetic behaviors of the individual drugs when administered in a conventional aqueous based cocktail, alter the administered ratio. This problem has been solved by using particulate delivery vehicles designed to coordinate drug delivery and release as described in PCT publication WO03/028696. The present invention offers an improvement that facilitates control in compositions that include paclitaxel and its analogs, as one or more additional antineoplastic agents can be formulated to mimic the pharmacokinetics of the taxane composition.

DISCLOSURE OF THE INVENTION

The present invention employs prodrugs of a taxane and micellar or nanoparticle delivery vehicles to facilitate pharmacokinetic control. By making the taxane more hydrophobic and consequently more compatible with lipid based delivery systems, the pharmacokinetics of the taxane compositions can be controlled. It is also possible to adjust the properties of formulations containing additional antineoplastic agents such that their effective release rates in vivo are matched to that of the taxane. Micelles or lipophilic nanoparticle carriers can be used to suspend these prodrugs and other agents in an aqueous environment.

As shown below, long circulating diglycolate prodrug nanoparticles provide significantly enhanced therapeutic activity over commercially formulated paclitaxel at the maximum tolerated dose; these types of formulations are therefore advantageous per se.

Thus, in one aspect, the invention is directed to a pharmaceutical composition which comprises nanoparticles or micelles formed from a prodrug of a taxane, which prodrug is a conjugate of said taxane coupled to a hydrophobic moiety through a glycolate linker wherein said prodrug is associated with a lipid and/or an amphiphilic stabilizer.

In other aspects, the invention is directed to methods to administer taxane using the compositions of the invention, to combine the compositions of the invention with formulations of additional antineoplastic agents and administer these and to methods of preparing these compositions and formulations.

BRIEF DESCRIPTION OF THE DRAWINGS

FIGS. 1A and 1B are graphs showing the elimination of test prodrugs 1 and 2 as measured by HPLC (FIG. 1A) or relative drug retention (FIG. 1B).

FIG. 4 shows the efficacy of prodrug 7 at various concentrations in comparison to Taxol™.

FIG. 5 shows the calculation of paclitaxel equivalents of prodrug 7 required to reach parity with Taxol™.

MODES OF CARRYING OUT THE INVENTION

Figure 2:
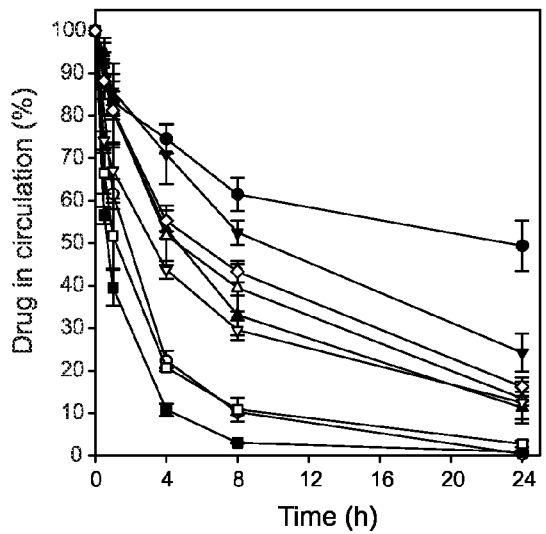
FIG. 2 shows the elimination of prodrugs 1-9 formulated in POPC/2kPS3k.

The invention provides compositions that show improved delivery characteristics for a taxane formulated as a prodrug being coupled through glycolate to a hydrophobic moiety. Because the pharmacokinetics of the formulation can be controlled by manipulating the nature of the hydrophobic moiety, as well as manipulating the components of the micelles or nanoparticles, desired characteristics of drug delivery can be achieved. These pharmacokinetics can be made to match the pharmacokinetics of formulations containing other antineoplastic agents, offering the opportunity for an improved system of coordinated drug delivery whereby the ratio of the antineoplastic agent and the taxane drug delivered to a tumor remains substantially that which is administered. Therefore, a synergistic ratio, determined in vitro, can be maintained within a factor of a little as 1.5 or 2 using the improved taxane formulation in combination with a compatible formulation of one or more additional antineoplastic agents. These formulations are useful, of course, in the treatment of cancer and other hyperproliferative indications. The maintenance of this ratio can readily be measured by determining the levels of the agents in blood or plasma over time. The coordinated compositions will maintain the administered ratio as measured in the blood or plasma within the foregoing limits over at least 1 hour or 4 hours or even 24 hours.

As noted above, the nanoparticulate or micellular components in the compositions of the invention that carry the taxane prodrug are composed of a lipid and/or an amphiphilic stabilizer.

As used herein, "taxane" refers to a class of drugs which consists of paclitaxel and its analogs. Paclitaxel was originally derived from the Yew tree and its analogs include docetaxel and other compounds of similar structure. Taxol™ is a commercially available form of paclitaxel formulated with Cremophor™.

The "hydrophobic moiety" that forms a part of the prodrug is generally a high molecular weight alcohol which can thus be coupled to the taxane through a glycolate linkage. The alcohol may be a straight, branched chain, or cyclic alcohol of 6 or more carbons, generally 6-30 carbons or, in some embodiments, 6-20 carbons. It may also be a steroid such as cholesterol or a tocopherol, such as vitamin E and related moieties.

The lipid that is associated with the prodrug in the nanoparticulate compositions of the invention is typically a phospholipid, such as distearoyl phosphatidylcholine, dipalmitoyl phosphatidylcholine, dimyristoyl phosphocholine, and corresponding phosphatidyl ethanols, phosphatidyl inositols, phosphatidyl glycerols, and the like. The fatty acid chains may also be unsaturated and include, for example, oleic and linoleic acids. The fatty acids need not be identical. In addition, the lipid moiety may be a sphingosine such as sphingomyelin or itself a tocopherol ester such as vitamin E succinate or vitamin E adipate.

The amphiphilic stabilizer is a polymeric compound comprising a hydrophilic portion and a hydrophobic portion. Typical hydrophobic polymers include polystyrene and hydrophobic derivatives of polymethacrylates as well as polyvinyl derivatives. Typical hydrophilic components include polyethylene glycol and hydrophilic derivatives of hydrophobic polymers, as well as dextran and dextran derivatives and polyamino acids. The list is meant to be exemplary and not exhaustive. In general, the amphiphilic stabilizer has a molecular weight greater than about 500 but may have a higher molecular weight of 1,000-50,000 g/mol.

In the examples below, a series of paclitaxel prodrugs designed for formulation in lipophilic nanoparticles is described. The hydrophobicity of paclitaxel was increased by conjugating a series of increasingly hydrophobic lipid anchors to the drug using succinate or diglycolate cross-linkers. While paclitaxel itself is nearly insoluble in water, it possesses sufficient aqueous solubility that it can rapidly partition out of lipid-based delivery systems, typically with half lives on the order of a few minutes. The present invention controls the pharmacokinetics of the formulated drug in vivo while maximizing efficacy. The prodrugs were formulated in well defined block copolymer stabilized nanoparticles. These nanoparticles were shown to have an elimination half-life of approximately 24 h in vivo. The rate at which the prodrug was released from the nanoparticles could be controlled by adjusting the hydrophobicity of the lipid anchor, resulting in release rates ranging from 1 to 24 h.

The nanoparticle formulations could be stored stably at 4° C. for several months.

To evaluate the therapeutic activity of the various paclitaxel prodrugs, nanoparticle formulations were administered intravenously into mice bearing HT29 human colon xenograph tumors. As the plasma half-life and area under the curve of the prodrug increased, activity against HT29 tumors also increased. Paclitaxel prodrug nanoparticles more than doubled the time for HT29 tumors to reach 400 mg relative to Taxol® when both treatments were administered at maximum tolerated dose (MTD) using the optimal treatment regimen for Taxol®.

Nanoparticle formulations of the type are most likely cleared as a result of single polymer chains partitioning out of the particle over time in vivo. Gradual loss of the stabilizer component destabilizes the particle and would result in the elimination of any payload that had not already partitioned out. Particles with a high drug/stabilizer ratio are cleared rapidly since the loss of relatively small amounts of polymer exposes the particle core to potential protein interactions. Particles with low drug/stabilizer ratios have greater tolerance to loss of polymer and survive long enough to be cleared through other mechanisms in vivo. An ideal delivery system should therefore approach the size of a micelle with a relatively low drug/polymer ratio, preferably with a stabilizer that has a low partitioning rate.

Prodrugs with lipid anchors of different hydrophobicity demonstrate different partition rates from the same particle composition. In these nanoparticles, drug physicochemical properties largely dictates the release of drug from the carrier, rather than degradation of the carrier itself. This behavior leads to a significant difference, for instance, between Taxol® and paclitaxel prodrugs in nanoparticles. Paclitaxel partitions rapidly out of cremophor micelles on injection and distributes broadly to lipophilic sinks it encounters in the blood compartment. Over time the drug redistributes back into the blood compartment before being eliminated. Prodrug nanoparticles do not exhibit this early distribution phase, but rather are continually releasing drug over time, the rate of which depends on the partitioning rate of the prodrug component. The prodrug partitioning rate was shown below to be directly correlated with efficacy, and this rate was readily tunable by varying the lipid anchor (and hence hydrophobicity) of the prodrug.

The dependence of efficacy on partitioning rate can be rationalized in terms of accumulation of nanoparticles in tumors followed by gradual release of prodrug. Nanoparticles that release their payload rapidly or are cleared rapidly from circulation will deliver less drug to the tumor site and consequently may be expected to exhibit reduced efficacy.

The compositions of the invention may further contain additional antineoplastic agents. As the pharmacokinetics of the taxane prodrug are readily controlled in the compositions of the invention, similar pharmacokinetics can be provided for the additional antineoplastic agent in either a similar composition or an alternative formulation and mixed with the composition of the invention or administered simultaneously to the subject. Thus, the additional antineoplastic agent may be formulated in liposomes, micelles, alternative nanoparticles, or other compositions designed to mimic the pharmacokinetics of the taxane. Suitable antineoplastic agents are of a wide variety and well known in the art and include, for example, the anthracyclines such as daunorubicin and doxorubicin, the platinum-containing drugs such as carboplatin and cisplatin, the family comprising irinotecan and its analogs, the fluoropyrimidines, and various other commonly employed agents such as methotrexate. The formulation of the additional antineoplastic agent (or agents), designed to mimic the pharmacokinetics of the taxane formulation can the be mixed with the taxane formulation as noted above, or administered substantially simultaneously as a separate composition.

In one embodiment, the taxane prodrugs can be co-formulated with hydrophobic prodrug analogues of water-soluble agents such as doxorubicin and dual-drug nanoparticles maintain the two agents at the injected drug:drug ratio in the plasma for extended times after injection. Formulating hydrophobic prodrugs in nanoparticles provides a novel approach to co-deliver anticancer drug combinations with widely differing physicochemical properties and maintain optimal drug:drug ratios in vivo.

The compositions of the invention can be administered by any suitable route; parenteral administration is preferred. Subjects to be treated include humans, other higher animals, and laboratory models, such as mice and rats.

The following examples are intended to illustrate but not to limit the invention.

EXAMPLES

Abbreviations: VES, Vitamin E succinate; POPC, 1-palmitoyl-2-oleoyl-sn-glycero-3-phosphocholine; CVIJ, confined volume impinging jets; 2 kPS3k, poly(ethylene glycol)$_{2000}$-b-polystyrene$_{3000}$; 2.5kPS3k, poly(ethylene glycol)$_{2500}$-b-polystyrene$_{3000}$; $^3$H—CHE, tritiated cholesterol hexadecyl ether; TLC, thin layer chromatography; DIPC, diisopropylcarbodiimide; DMAP, N,N-4-dimethylaminopyridine.

Materials. All reagents unless otherwise specified were purchased from Sigma-Aldrich Canada Ltd., Oakville, ON. Solvents were obtained from VWR International, Mississauga, ON. Paclitaxel was purchased from Indena S.p.A., Milan, Italy. $^3$H—CHE was obtained from Perkin Elmer Life and Analytical Sciences, Inc., Waltham, Mass. POPC was obtained from Northern Lipids, Burnaby, BC. $^1$H NMR spectra were recorded in CDCl$_3$ on a Bruker Advance 400. HT-29 Human colorectal adenocarcinoma cells were obtained from ATCC, Manassas, Va. Foxn1$^{nu}$ mice were obtained from Harlan, Indianapolis, Ind. The confined volume impinging jets mixer was custom built at Princeton University. All animal experiments were conducted according to protocols approved by the University of British Columbia's Animal Care Committee and in accordance with the current guidelines established by the Canadian Council of Animal Care.

Example 1

Synthesis of Prodrug

A range of commonly available lipid alcohols were used as the anchor component (Scheme 1), including α-tocopherol (1 and 3), oleyl alcohol (2 and 4), octadecanol (5), cosanol (6), docosanol (7), cholesterol (8) and 1,2-dimyristoyl-sn-glycerol (9). The lipids were conjugated to the cross-linker by treatment with the corresponding cyclic anhydride, followed by condensation of the anchor-linker product with paclitaxel using diisopropylcarbodiimide (DIPC) in the presence of N,N-4-dimethylaminopyridine (DMAP). Succinic acid (1-2) and diglycolic acid (3-9) were used as the cross-linkers. The 3-oxa moiety of the latter was intended to increase the susceptibility of the 2'-acyl group of the cross-linker to hydrolysis relative to the succinate analogues.

Scheme 1. Synthesis of lipophilic paclitaxel prodrugs

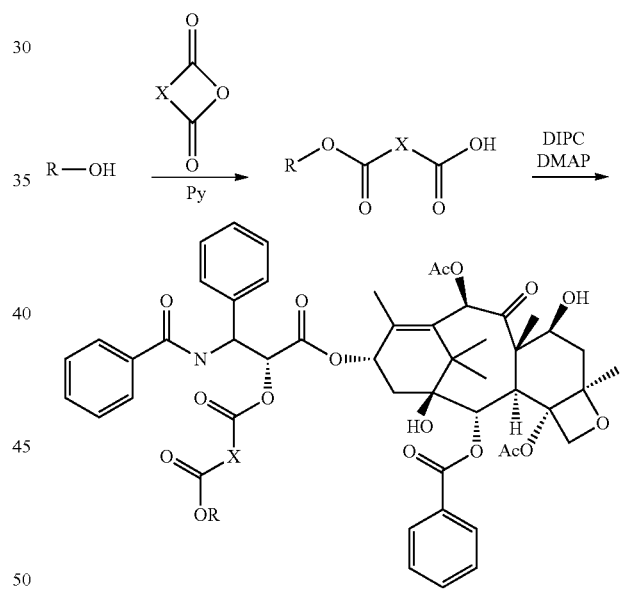

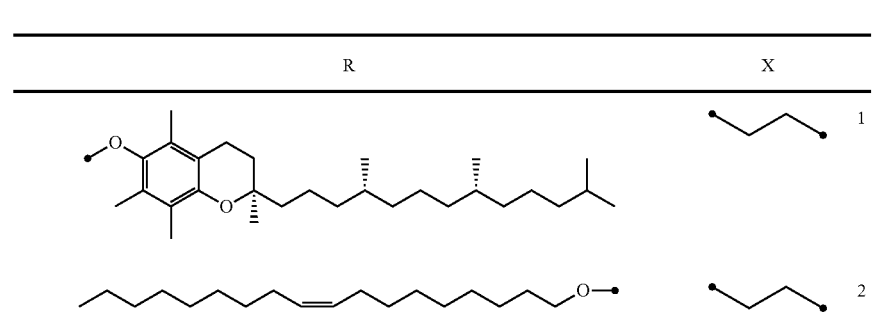

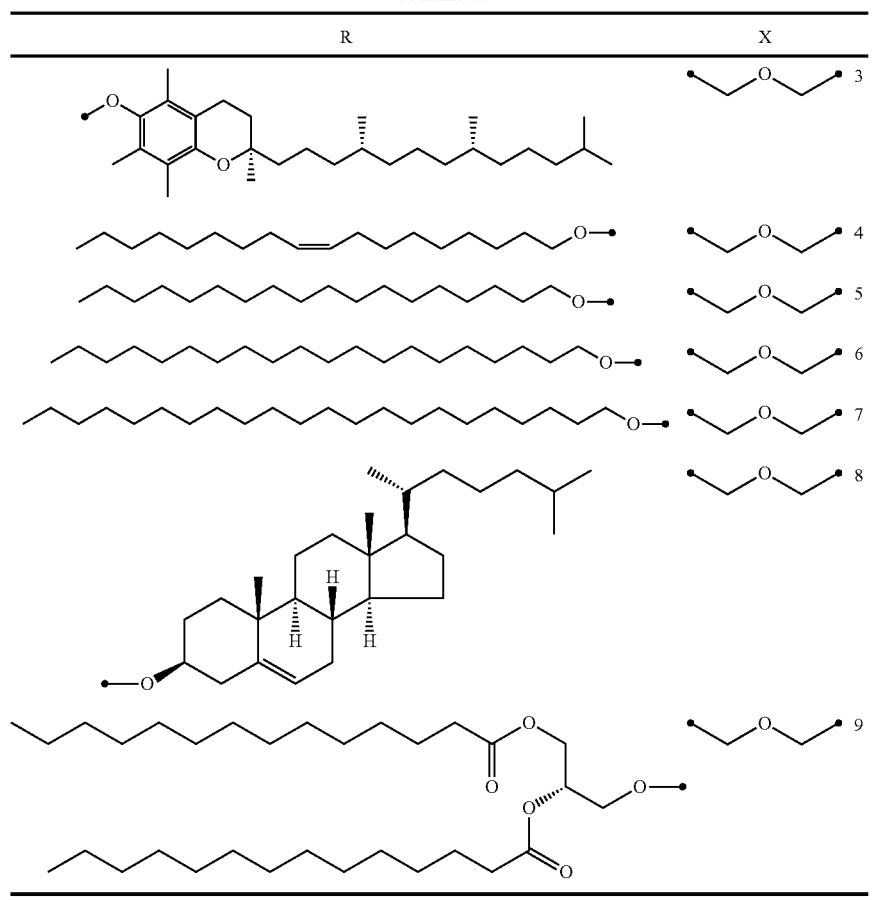

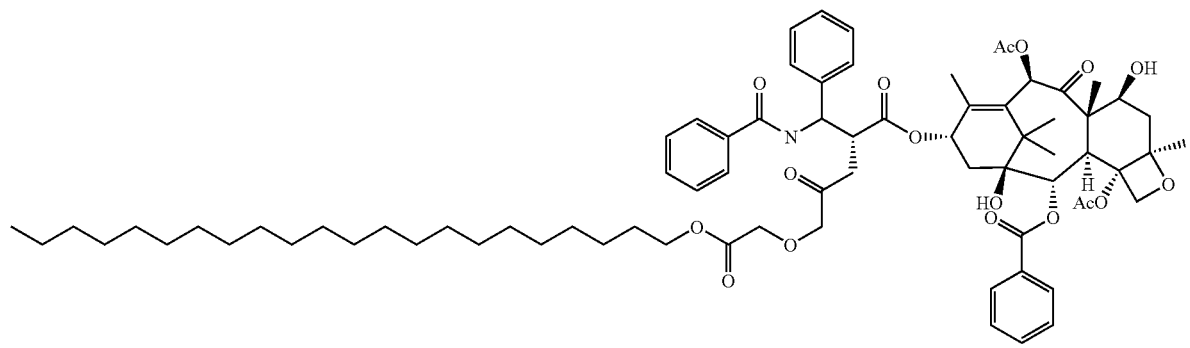

SYNOPSIS TOC

The 2'-acyl paclitaxel derivatives were prepared selectively by exploiting the difference in reaction rates between the paclitaxel 2'- and 7-hydroxyl groups. Under the reaction conditions used here, the majority of paclitaxel was consumed before significant levels of the 2',7-diacyl product were generated, as monitored by TLC. Column chromatography was used to remove unreacted paclitaxel, the 2',7-diacyl product and other impurities in the crude reaction mixture. Purity and identity of the final products were confirmed by HPLC and NMR analysis, respectively.

For synthesis of the lipid anchors, a lipid alcohol in pyridine was treated with 3 equivalents of succinic anhydride or diglycolic anhydride at room temperature overnight. The solvent was removed on a roto-vap and the residue extracted from dilute hydrochloric acid with methylene chloride. The organic fractions were dried over anhydrous magnesium sulphate, filtered and the solvent was removed. Conversion to the appropriate acid was monitored by TLC, which in most cases was 100%. The resultant product was either dried under vacuum or lyophilized from benzene. The lipid acids were used in the following steps without further purification.

For synthesis of the paclitaxel conjugates, paclitaxel (1 equiv), a lipid acid (2 equiv) and 4-N,N-dimethylaminopyridine (3 equiv) were dissolved in alcohol free chloroform. Diisopropylcarbodiimide (1.3 equiv) was then added and the solution stirred at room temperature. The reaction was monitored by TLC until most of the paclitaxel had been consumed (typically 2-4 h). The reaction mixture was then washed with dilute hydrochloric acid and dried over anhydrous magnesium sulfate. After removal of solvent the crude product was passed down a silica gel column using a methanol/methylene chloride gradient. The purified prodrug was lyophilized from benzene and stored at room temperature.

The prepared compounds are:

2'-O-(4"-O-tocopherylsuccinoyl)-paclitaxel 1. Synthesized from paclitaxel and tocopherol succinate. $^1$H NMR (400 MHz, CDCl$_3$) δ 3.83 (1H, d, J=7.25 Hz); 4.22 (1H, d, J=8.60 Hz); 4.33 (1H, d, J=8.60 Hz); 4.46 (1H, dd, J=10.88 Hz, J'=6.58 Hz); 4.99 (1H, d, J=9.54 Hz); 5.52 (1H, d; J=3.22 Hz); 5.70 (1H, d, J=6.98 Hz); 5.98 (1H, dd, J=9.13 Hz, J'=3.22 Hz); 6.27 (1H, t, J=8.6 Hz); 6.97 (1H, d, J=8.87 Hz).

2'-O-(4"-O-oleylsuccinoyl)-paclitaxel 2. Synthesized from paclitaxel and oleyl succinate. $^1$H NMR (400 MHz, CDCl$_3$) δ 3.82 (1H, d, J=7.0 Hz); 3.96 (2H, t, J=6.81 Hz); 4.21 (1H, d, J=8.38 Hz); 4.33 (1H, d, J=8.38 Hz); 4.46 (1H, br. s); 4.98 (1H, d, J=8.45 Hz); 5.36 (2H, m); 5.50 (1H, d, J=2.89 Hz); 5.69 (1H, d, J=7.00 Hz); 6.00 (1H, dd, J=9.04 Hz, J'=2.74 Hz); 6.26 (1H, t, J=8.91 Hz); 7.08 (1H, d, J=9.06 Hz).

2'-O-(5"-O-tocopheryldiglycoloyl)-paclitaxel 3. Synthesized from paclitaxel and tocopherol diglycolate. $^1$H NMR (400 MHz, CDCl$_3$) δ 3.84 (1H, d, J=6.98 Hz); 4.22 (1H, d, J=8.3 Hz); 4.34 (1H, d, J=8.6 Hz); 4.99 (1H, d, J=7.79 Hz); 5.64 (1H, d, J=2.96 Hz); 5.70 (1H, d, J=6.98 Hz); 6.06 (1H, dd, J=9.27 Hz, J'=2.82 Hz); 6.30 (1H, t); 6.97 (1H, d, J=9.13 Hz).

2'-O-(5"-O-oleyldiglycoloyl)-paclitaxel 4. Synthesized from paclitaxel and oleyl diglycolate. $^1$H NMR (400 MHz, CDCl$_3$) δ 3.83 (1H, d, J=7.0 Hz); 4.46 (1H, t, J=7.96 Hz); 4.99 (1H, d, J=8.45 Hz); 5.35 (2H, m); 5.60 (1H, d, J=2.74 Hz); 5.70 (1H, d, J=7.08 Hz); 6.05 (1H, dd, J=9.25 Hz, J'=2.55 Hz); 6.28 (1H, t, J=8.9 Hz); 7.04 (1H, d, J=9.29 Hz).

2'-O-(5"-O-octadecyldiglycoloyl)-paclitaxel 5. Synthesized from paclitaxel and octadecyl diglycolate. $^1$H NMR (400 MHz, CDCl$_3$) δ 3.83 (1H, d, J=7.0 Hz); 4.46 (1H, dd, J=10.74 Hz, J'=6.70 Hz); 4.99 (1H, d, J=8.45 Hz); 5.60 (1H, d, J=2.82 Hz); 5.70 (1H, d, J=7.00 Hz); 6.05 (1H, dd, J=9.25 Hz, J'=2.55 Hz); 6.28 (1H, t, J=8.9 Hz); 7.05 (1H, d, J=9.29 Hz).

2'-O-(5"-O-cosanyldiglycoloyl)-paclitaxel 6. Synthesized from paclitaxel and cosanyl diglycolate. $^1$H NMR (400 MHz, CDCl$_3$) δ 3.83 (1H, d, J=6.98 Hz); 4.0-4.4 (5H, m); 4.46 (1H, dd, J=10.75 Hz, J'=6.72); 4.99 (1H, d, J=9.40 Hz); 5.60 (1H, d, J=2.96 Hz); 5.70 (1H, d, J=7.25 Hz); 6.05 (1H, dd, J=9.27 Hz, J'=2.82); 6.29 (1H, t, J=8.3 Hz); 7.05 (1H, d, J=9.13 Hz).

2'-O-(5"-O-docosanyldiglycoloyl)-paclitaxel 7. Synthesized from paclitaxel and docosanyl diglycolate. $^1$H NMR (400 MHz, CDCl$_3$) δ 3.83 (1H, d, J=6.98 Hz); 4.0-4.4 (5H, m); 4.46 (1H, dd, J=10.75 Hz, J'=6.72 Hz); 4.99 (1H, dd, J=9.40 Hz, J'=1.61 Hz); 5.60 (1H, d, J=2.96 Hz); 5.70 (1H, d, J=6.98 Hz); 6.05 (1H, dd, J=9.40 Hz, J'=2.95 Hz); 6.28 (1H, t, J=8.3 Hz); 7.05 (1H, d, J=9.40 Hz).

2'-O-(5"-O-cholesteryldiglycoloyl)-paclitaxel 8. Synthesized from paclitaxel and cholesteryl diglycolate. $^1$H NMR (400 MHz, CDCl$_3$) δ 3.83 (1H, d, J=x Hz); 4.0-4.4 (5H, m); 4.47 (1H, dd, J=10.6 Hz, J'=6.8 Hz); 4.63 (1H, m); 4.99 (1H, d, J=7.79 Hz); 5.38 (1H, d, J=3.76 Hz); 5.61 (1H, d, J=2.69 Hz); 5.70 (1H, d, J=7.25 Hz); 6.06 (1H, dd, J=9.13 Hz, J'=2.69 Hz); 6.28 (1H, t, J=8.3 Hz); 7.09 (1H, d, J=9.40 Hz).

2'-O-(5"-O-(1''',2'''-dimyristoyl-sn-glycero)diglycoloyl)-paclitaxel 9. Synthesized from paclitaxel and 3-(1,2-dimyristoyl-sn-glycerol) diglycolate. $^1$H NMR (400 MHz, CDCl$_3$) δ 3.84 (1H, d, J=6.98 Hz); 4.47 (1H, dd, J=10.6 Hz, f=6.8 Hz); 4.99 (1H, dd, J=9.54 Hz, J'=1.75 Hz); 5.20 (1H, m); 5.61 (1H, d, J=2.96 Hz); 5.71 (1H, d, J=7.25 Hz); 6.07 (1H, d, J=9.27 Hz, J'=2.82 Hz); 6.31 (1H, t); 7.11 (1H, d, J=9.40 Hz).

Example 2

Nanoparticle Formulation

The prodrug, co-lipid and stabilizer polymers (typically on a 1:1:2 w/w basis) were dissolved in ethanol/THF (4:1) at a concentration of 40 mg/ml. The solvent was rapidly diluted with water using a four port CVIJ mixer[13, 14] with flow rates set at Dec. 12, 1953/53 ml/min (solvent/water/water/water). Flow rates were controlled using Harvard Apparatus PHD2000 syringe pumps. The resultant solution was then dialyzed against water to remove residual solvent. The final drug concentration was typically about 0.7 mg/ml. When higher concentrations were required the dialyzed solution was diluted with equi-volumes of 600 mM sucrose and then concentrated using a 100 kD, 0.5 mm lumen, 60 cm path length MidGee hoop cartridge (GE Healthcare Life Sciences, Piscataway, N.J.) with a peristaltic pump. Particle size was determined using a Malvern Zetasizer Nano-ZS particle sizer and reported as volume weighted data.

Formulations were composed of a prodrug, a co-lipid and an amphipathic stabilizer in a weight ratio of 1:1:2, respectively at a concentration of 40 mg per mL of solvent. The use of higher initial concentrations (>40 mg/mL) often led to the generation of large particles that compromised downstream handling of the preparation. The co-lipids were either α-tocopherol-succinate (VES) or POPC which facilitated processing. VES was replaced by POPC in later formulations since VES precipitated on long term storage at 4° C. Poly(ethylene glycol)-b-polystyrene (2kPS3k or 2.5kPS3k) was used as the amphipathic stabilizer. Other stabilizers may also be used. Using the flash precipitation procedure, the mean particle diameter ranged from 10-20 nm for the prodrug/VES/2kPS3k nanoparticles, and 20-30 nm for the prodrug/POPC/2kPS3k nanoparticles.

The stability of nanoparticle formulations was monitored by HPLC after long-term storage at 4° C.

Samples containing (50 μL) of nanoparticles were mixed with 150 μL of diluents (methanol:acetonitrile, 2:1 v/v) by vigorous vortexing followed by centrifugation at 10000×g for 10 minutes. Supernatant (20 μL) was injected into a Waters HPLC for quantitation using a Phenomenex SynergiFusion reverse phase analytical column monitored by UV detection at 227 nm. Chromatography was conducted with a 1 mL/min gradient elution of methanol and 10 mM sodium acetate buffer (pH 5.6) mobile phases from an initial solvent mix of 70:30 to 100:0 respectively. Column temperature was set at 30° C. Samples were kept in the autosampler compartment at 4° C. prior to HPLC analysis.

Analysis of 4, 5 and 6 formulated with POPC/2kPS3k (1:1:2) in unbuffered 300 mM sucrose showed less than 5% free paclitaxel present after 11 weeks of storage. Free drug at that level was shown to have no antitumor activity in control efficacy experiments (data not shown). Accordingly, stability was considered adequate for the in vivo experiments carried out in these investigations.

Nanoparticle formulations stored in either sucrose solution or water at 4° C. were found to be physically stable for three months by visual inspection, with the exception of 8 which formed precipitates in some formulation compositions after 1-2 weeks of storage. Formulations using VES as the co-lipid also led to the slow formation of colloidal or crystalline precipitates, likely due to VES partitioning to the aqueous phase followed by subsequent precipitation outside the nanoparticle. VES formulations were therefore only suitable for short term studies and not for longer term experiments such as efficacy evaluations.

The physical stability of formulations was investigated by examining changes in particle size after vortexing prodrug/co-lipid/2.5kPS3k (1:1:2) nanoparticles in water, 150 mM saline or 300 mM sucrose (Table 1). These formulations consisted primarily of nanoparticles with diameters between 20 and 30 nm. Particles that were sensitive to mechanical stress underwent aggregation or phase separation when subjected to these conditions, resulting in the formation of larger particles in the sample. The increase in particle size was monitored by using dynamic light scattering to measure the Z average (the intensity weighted mean size of the particle distribution) value for samples before and after vigorous vortexing. The change in the $Z_{ave}$ value was used as surrogate readout for the formation of aggregates or precipitates resulting from mechanical instability, where a higher value for $\Delta Z_{ave}$ indicated a higher level of aggregation or precipitation (Table 1). Nanoparticles with POPC as the co-lipid were found to be significantly more stable in the presence of salt than those prepared with VES or in the absence of a co-lipid ($\Delta Z_{ave}$=24, 372 and 774 nm respectively for formulations of 5). In most cases mechanical stability was significantly improved in the presence of 300 mM sucrose compared to water. Sucrose samples where $\Delta Z_{ave}$ was in the range 0-40 nm had very little or no micron-sized material (<2% of the sample). Some prodrug formulations (3 and 9) which generated higher levels of aggregation in water and saline under these conditions ($\Delta Z_{ave}$=100-200 nm) were stable in sucrose ($\Delta Z_{ave}$=0-40 nm). The conclusion of the study was that the best stability was obtained using POPC co-lipids in nanoparticles formulated in 300 mM sucrose.

TABLE 1

Physical stability of prodrug formulations. All formulations were prepared as prodrug/co-lipid/2.5kPS3k (1:1:2) nanoparticles in water. Particle diameter is the volume weighted average as determined with a Malvern Nano-ZS particle sizer. Stability was assessed by measuring the change in the $Z_{ave}$ ($\Delta Z_{ave}$) of samples diluted with equi-volumes of water, 300 mM saline or 600 mM sucrose after vortexing for 30 seconds.

| Prodrug | Co-lipid | Diameter (nm) | $\Delta Z_{ave}$ (nm) water | $\Delta Z_{ave}$ (nm) 150 mM saline | $\Delta Z_{ave}$ (nm) 300 mM sucrose |
|---|---|---|---|---|---|
| 2 | POPC | 26 | 20 | 43 | 10 |
| 3 | POPC | 24 | 125 | 55 | 42 |
| 4 | POPC | 22 | 15 | 25 | 5 |
| 5 | POPC | 21 | 20 | 24 | 7 |
| 6 | POPC | 23 | 21 | 26 | 36 |
| 7 | POPC | 23 | 18 | 24 | 0 |
| 8 | POPC | 23 | 47 | 42 | 41 |
| 9 | POPC | 23 | 167 | 171 | 0 |
| 5 | VES | 7 | 3 | 372 | 10 |
| 5 | — | 28 | 109 | 774 | 71 |

Similar results were obtained when samples were subjected to normal processing steps required for large sample preparations. Nanoparticles formulated in water or with either VES or no co-lipid were not stable when exposed to mechanical stress and exhibited significant precipitate formation during concentration steps using diafiltration. Stability while concentrating formulations could be improved by diluting the nanoparticle solution with sucrose for a final concentration of 300 mM prior to concentration. Use of POPC as the co-lipid provided further improvement of physical stability during storage and post-formation processing, consistent with the results of the earlier stability studies. All of the concentrated samples used in this work subsequently were based on POPC as a co-lipid and were prepared in 300 mM sucrose. Under these conditions precipitate formation was negligible up to drug concentrations of 8 mg/mL.

The diglycolate linkage was found to be more susceptible to hydrolysis over the succinate linkage, as may be predicted based on the relative lability of the ester linkages. The increased reactivity of the diglycolate linkage posed an additional difficulty for accurate analysis of prodrug in biological samples. Methanol:acetonitrile 1:4 (v:v) was effective in near complete precipitation of plasma proteins and liberation of the prodrug from the nanoparticle. However, a steady increase of free paclitaxel over time was observed after processing plasma samples, indicating hydrolysis during matrix workup and HPLC analysis. The diglycolate prodrug 6 was completely hydrolyzed after 9 hours while the succinate prodrug 2 was reduced to approximately 25% after 68 hours. Hydrolysis was not observed when the samples were buffered with acetate at pH 4. Unbuffered samples of 6/POPC/2kPS3k in the absence of plasma did not exhibit this hydrolysis, indicating that the time-dependent hydrolysis of prodrug in these formulations was most likely due to the presence of a non-precipitated plasma component. This result suggests that the prodrug is stable when it is in the particle, and that hydrolysis in biological media takes place after release of the prodrug.

Example 3

In Vitro Activity

The MCF-7 human tumor cell line was purchased from American Type culture Collection (Manassas, Va.). The A2780 human tumor cell line was purchased from the European Collection of Cell culture (UK).

Cells were exposed in triplicates to a serial dilution of prodrug/POPC/2.5kPS3k (1:1:2) nanoparticle formulations for 72 hours at 16 concentrations. Viable cells were quantified using standard 3-(4,5-dimethylthiazol-2-yl)-2,5-diphenyltetrazolium bromide (MTT) detection at 570 nm after DMSO addition. Survival rate after treatment is expressed as a mean percentage relative to untreated control wells.

Evaluation of prodrug cytotoxicity was carried out using A2780 and MCF-7 human tumor cells treated with prodrug/POPC/2.5kPS3k (1:1:2) formulations prepared in distilled water (Table 2). Control formulations containing no prodrug confirmed that other nanoparticle components did not contribute to the growth inhibition of the cells. In addition, 1 was evaluated using a number of different nanoparticle formulations (1/VES/2kPS3k; 1/2 kPS3k and 1/cremophor) to show that the observed activity was independent of the type of formulation used.

TABLE 2

Inhibition of human tumor cell lines using prodrug/POPC/2kPS3k (1:1:2) formulations.

| | $IC_{50}$ values (nM ± SD) | |
|---|---|---|
| Compound | A2780 | MCF-7 |
| Paclitaxel | 2.4 ± 0.3 | 3.8 ± 0.6 |
| 1 | 192 ± 18 | 158 ± 72 |
| 2 | 75.1 ± 3.9 | 67.0 ± 5.9 |
| 3 | 25.3 ± 1.3 | 13.4 ± 2.4 |
| 4 | 28.4 ± 1.4 | 15.9 ± 0.7 |
| 5 | 20.9 ± 10.9 | 1.1 ± 1.5 |

TABLE 2-continued

Inhibition of human tumor cell lines using prodrug/POPC/2kPS3k (1:1:2) formulations.

| Compound | IC$_{50}$ values (nM ± SD) | |
| --- | --- | --- |
|  | A2780 | MCF-7 |
| 6 | 29.0 ± 1.3 | 16.6 ± 4.5 |
| 7 | 29.5 ± 5.2 | 23.5 ± 1.3 |
| 8 | 27.0 ± 1.1 | 24.1 ± 0.6 |
| 9 | 34.7 ± 1.3 | 32.2 ± 1.3 |

Succinate-linked prodrugs (1 and 2) were found to be ~1-2 orders of magnitude less potent than free paclitaxel against A2780 and MCF-7 cells. This trend was observed in most cell lines tested. The decrease in observed activity was likely the result of resistance of the succinate group to hydrolysis. Subsequent prodrugs (3-9) were prepared with the diglycolate linker moiety which was expected to be more susceptible to hydrolysis due to the presence of the 3-oxa group. The diglycolate prodrugs all showed similar potency in growth inhibition assays (~20 nM) and were an order of magnitude less potent than paclitaxel positive controls. The succinate analogs were always less potent than the corresponding diglycolate prodrugs. For example, in the A2780 cell line the IC$_{50}$ values for the succinate prodrug 1 and diglycolate prodrug 3 were 192 nM and 25.3 nM, respectively, compared to 2.4 nM for paclitaxel. Likewise the succinate 2 and diglycolate 4 had IC$_{50}$ values of 75.1 and 28.4 nM respectively. These results are consistent with literature reports of related compounds, where IC$_{50}$ values in the MCF-7 breast carcinoma cell line for paclitaxel, 2'-O-hexadecanoylpaclitaxel and 2'-(2''-bromohexadecanoyl)paclitaxel were reported as <1, 8600 and 70 nM respectively.[7]

Example 4

In Vivo Nanoparticle Plasma Elimination

Athymic nude mice (n=3/timepoint) were injected iv with test samples (10 µl/g body weight, to a maximum of 250 µl). Blood was collected at the designated time point by cardiac puncture and placed into EDTA coated microtainer tubes (BD Biosciences). The tubes were centrifuged at 2800 rpm for 10 minutes. Plasma was recovered and 50 µl aliquots analyzed by HPLC for drug content. Samples containing $^3$H—CHE (50 µl) were diluted with PicoFluor40™ scintillation fluid (Packard) and counted on a Beckman-Coulter LS 6500 Multipurpose scintillation counter. The total drug (counts) per mouse in the blood compartment was calculated assuming a plasma volume of 0.04125 mL per gram of body weight.

Partitioning rates for lipophilic drugs from lipid based particle formulations are commonly determined by dialysis of the drug carrier system against a bulk aqueous phase. The low aqueous solubility of the drug under these circumstances results in a high probability of the drug partitioning back into the carrier system rather than eluting through the dialysis membrane, resulting in artificially low apparent partitioning rates. Such an experiment does not accurately reflect behavior observed for hydrophobic drugs in vivo, where free drug can rapidly partition into the large hydrophobic reservoir present (for example, cell membranes or lipophilic proteins) rather than back into the delivery vehicle. Dialysis experiments therefore misrepresent the true delivery capability of these formulations. The most accurate means of determining true partitioning rates in vivo is to track both the drug and the particle using a non-exchangeable marker. Consequently it was necessary to identify such a marker and to confirm that it reflected the particle pharmacokinetics.

Elimination studies tracking both the prodrug and the particle were conducted to obtain a more accurate description of the partitioning behavior of the prodrugs in vivo (FIG. 1). Prodrug elimination was followed by HPLC, while particle elimination rates were determined by labeling nanoparticles with tritiated cholesterylhexadecyl ether (3H—CHE). This label is widely used to track liposomes in vivo since it is regarded as a non-exchangeable, non-metabolizable lipid marker in those systems. It was expected that the hydrophobicity and low level of hydration of this molecule would result in low partitioning rates from the nanoparticles used in this study, and therefore would provide an assessment of particle fate, provided that particle integrity was maintained.

A number of experiments were carried out to determine the validity of the above assumptions and approximate the particle plasma elimination rate. Formulations comprised of 1/VES/2kPS3k (1:1:2) and 2/VES/2kPS3k (1:1:2) were labeled with trace amounts of $^3$H—CHE and plasma levels of both the label and prodrug were monitored in Foxn1$^{nu}$ mice (FIG. 1, Panel A). The $^3$H—CHE label cleared at the same rate in both groups, with a half life of approximately 24 h. Prodrug 1 cleared at approximately the same rate as $^3$H—CHE in this system, while 2 was cleared significantly faster. Comparison of prodrug/$^3$H—CHE ratios (FIG. 1, Panel B) demonstrated that the ratio of 1 to particle label was virtually unchanged over the course of the experiment, suggesting that the partitioning half life was significantly longer than the duration of the experiment. Prodrug 2 decreased relative to $^3$H—CHE at a rate consistent with a partitioning half life of approximately 4 h. The data in the experiment could be fitted to a four parameter double exponential decay implying that the partitioning rate constant changed over time, presumably in response to local environmental changes as drug partitioned out of individual particles.

The effects of formulation composition on elimination were determined by comparing the plasma elimination of 1 and $^3$H CHE using 1/2kPS3k, 1/POPC/2kPS3k and $^3$H—CHE labeled 1/VES/2kPS3k (1:1:2) formulations in vivo (data not shown). For all three formulations both the label and prodrug elimination rates were found to be similar to that observed for 1 in FIG. 1, indicating little to no role of co-lipid on the rate of elimination of 1 in these formulations. Additional elimination studies were performed using $^3$H—CHE labeled 2kPS3k micelles and POPC/2kPS3k (1:2) nanoparticles, neither of which contained prodrug (data not shown). In both cases the $^3$H—CHE label was cleared at approximately the same rate as observed for 1 in FIG. 1. Finally, studies using 1/VES/3kPS3k and 1/VES/2.5kPS1.6k formulations showed that moderate variations in the stabilizer poly(ethylene glycol)/polystyrene ratio had little effect on the elimination of 1 relative to that seen in FIG. 1 (data not shown).

Elimination of 1 in these formulations was found to be independent of co-lipid and stabilizer composition, and corresponded to the loss of the $^3$H—CHE marker over time. These results suggest that the $^3$H—CHE label remains with the particle throughout the pharmacokinetic experiment, independent of changes in the composition of the particle. The circulation half lives for these particles were notably long (approximately 24 hours), an order of magnitude longer than has been reported for micelles prepared using other polymers at these concentrations and comparable to that observed with long-circulating liposomes.

Effect of prodrug partitioning on plasma drug elimination was determined. The prodrug panel was screened using prodrug/POPC/2kPS3k (1:1:2) nanoparticles in Foxn1$^{nu}$ mice to determine elimination rates for the different prodrug conjugates (FIG. 2). Prodrug circulation levels appeared to be dependent primarily on the prodrug partitioning rate, and consequently indirectly reflect that rate, since the particles are sufficiently stable to remain intact over the course of the experiment. Conjugates were formulated at a concentration of 0.7 mg/mL. Variations in concentration did not appear to affect the particle elimination rate since the plasma elimination of 1/VES/2.5kPS1.6k (1:1:2) was largely independent of dose over the range 3-25 mg/kg (data not shown).

In order to estimate the partitioning half-life for each prodrug, it was assumed that 1 tracked the particle elimination rate based on the results discussed above. The elimination of all other prodrugs were then fitted to four parameter double exponential decay curves and normalized against 1. The presence or absence of prodrug in the formulation did not significantly affect the elimination behavior of the particles, implying that changes in composition over time as drug partitioned out did not affect particle elimination rates. Prodrug elimination normalized to 1 therefore yielded a reasonable approximation of the relative partitioning half lives of the prodrugs in these formulations.

Prodrug 1 had a negligible partitioning rate over 24 h whereas 2 in this composition partitioned out with a half life of approximately 1.7 h. Both of these prodrugs used succinate cross linkers and were significantly less active than paclitaxel in vitro. The diglycolate versions of these compounds (3 and 4 respectively) showed accelerated elimination relative to their succinate parents, with partitioning half lives of approximately 13 h and 1 h, respectively. This is consistent with an increased level of hydration on partitioning into the aqueous phase due to the presence of the 3-oxa group of the diglycolate linkage.

The effect of small changes to the size of the lipid anchor was determined using the series 4, 5, 6 and 7, which have oleyl (ΔC18), stearyl (C18), cosanyl (C20) and docosanyl (C22) moieties, respectively. Based on the results in FIG. 2 we estimated the partitioning half lives for these prodrugs to be approximately 1 h, 1.7 h, 6.5 h and 10 h, respectively. These results indicate that prodrug release from the nanoparticles can be regulated by adjusting the length of the alkyl anchor used.

The effect of other common lipid types on partitioning kinetics was also examined. A cholesteryl diglycolate conjugate (8) was retained considerably longer than the straight chain aliphatic species, with an estimated partitioning half-life of approximately 21 h. Unfortunately 8 was susceptible to phase separation from nanoparticles on storage and was not fully evaluated in later efficacy studies in this work. A 1,2-dimyrsistoyl-sn-glycero-3-succinate derivative (9) was evaluated in anticipation that it would be better retained than 7 since it had two C14 anchors, however it partitioned out faster, with a half-life of 8.5 h. The higher partitioning rate was likely due to increased levels of hydration on the glycerol backbone during exchange out of the nanoparticle.

Example 5

In Vivo Efficacy

Female athymic nude mice (7-8 weeks old) were inoculated subcutaneously with 100 µl HT29 human colon carcinoma cells (2×10$^6$ cells) using a 26 gauge needle. Mice were randomly grouped (n=6/group) with a mean tumor size between 80 and 120 mg prior to first treatment. (Tumors greater than 200 mg and smaller than 30 mg were excluded.) Test samples were injected with a volume of 10 µl drug/g body weight, to a maximum of 250 µl. Subsequent injections were made according to the designated schedule. Tumor length and width measurements, body weight and in life observations were recorded 2-3 times per week. Tumor weight was calculated according to the formula $(L \times W^2)/2$.

Figure 3:
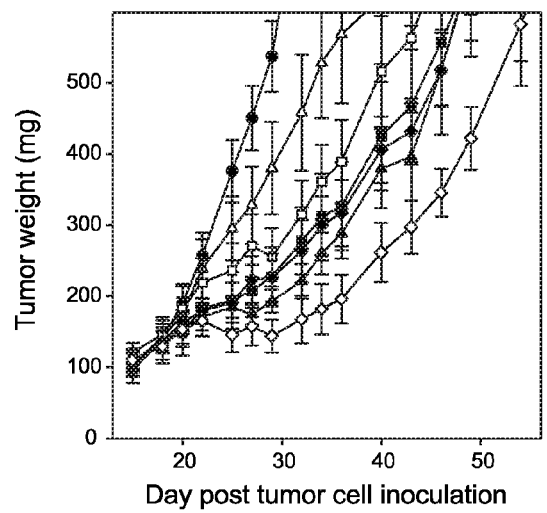
FIG. 3 shows the relative efficacy of prodrugs 1-7 in a similar formulation.

The relative efficacies of nanoparticle formulations of 1, 2, 4, 5, 6 and 7 were determined in the HT29 model using a 36 µmol/kg dose on a Q4Dx6 schedule (FIG. 3). Saline was used as a negative control. Earlier experiments conducted with sub-maximal doses suggested that this dose would result in a range of responses bracketing the behaviors of positive and negative control groups, and in this way would allow discernment of the relative therapeutic potencies of the individual prodrug species. Prodrug 8 was not included in the study due to precipitation of drug from formulations on storage. Prodrugs 3 and 9 were omitted as well since their partitioning half lives were similar to 6 and 7.

The two succinate linked prodrugs, 1 and 2, showed no evidence of any therapeutic activity at the 34 µmol/kg dose. The results correlated with the observation that these prodrugs were 1-2 orders of magnitude less potent than paclitaxel in in vitro cell growth inhibition assays (Table 2). The partitioning half lives of 2 and 1 differed widely, ranging from 1.7 h with 2 to effectively non-exchangeable on experimental timeframes with 1. These results indicate that even though the succinate-linked species 2 is being made available to cells, the lower hydrolysis rate and concomitant release of paclitaxel is insufficient to provide a meaningful therapeutic response.

Preliminary in vivo particle distribution studies indicated tumor accumulation levels plateau at ~3% of the injected dose per gram of tumor tissue, with the majority of the accumulation occurring within the first 8 h. Similar results have been reported in the literature. In the case of prodrugs such as 4 and 5 where partitioning half lives are approximately 1 and 1.7 h respectively, the level of drug delivered to tumors is expected to be significantly lower, likely accounting for the reduced efficacy observed for these species. Prodrugs 6 and 7 release drug at slower rates, with partitioning half lives of approximately 6.5 and 10 h respectively. Since the particle accumulation in tumor is expected to be similar in all cases, formulations with these prodrugs are capable of delivering more drug to the tumor.

The four diglycolate linked species, 4, 5, 6 and 7, all resulted in varying degrees of inhibition of tumor growth. In vitro growth inhibition studies of these prodrugs had demonstrated that the cytotoxicity of diglycolate-linked prodrugs was greater than their succinate analogs (Table 2). Elimination data for these formulations indicated that aliphatic chain length was related to partitioning half lives for the prodrugs, which were 1 h, 1.7 h, 6.5 h and 10 h, respectively. This correlates well with the observed efficacy trends, where the greatest antitumor response is seen with the prodrug having the longest partitioning half life, namely the docosanyl conjugate 7. Relative efficacy was determined using the treatment induced delay in reaching a mean tumor size of 500 mm$^3$, yielding values of 3, 4, 15 and 17 days, respectively. Based on these results, further investigations to optimize dose and scheduling using the nanoparticle formulation of 7 were undertaken.

Example 6

Effect of Dose on the Efficacy of 7

The activity of 7 in POPC/2.5kPS3k nanoparticle formulations relative to paclitaxel was determined by comparing the efficacy of doses ranging from 0.25 to 3 mole equivalents of paclitaxel (FIG. 4) in the HT29 tumor model. Taxol® dosed at 23 µmol/kg on a Q2Dx5 schedule was used as a positive control. The dosing regime was chosen since the greatest efficacy for 7 was observed on a Q2D schedule, which was also optimal for Taxol®, and the maximum tolerated treatment course at this Taxol® dose was 5 injections. The maximum tolerate dose of 7 on this schedule was approximately 3 paclitaxel equivalents (69 µmol/kg).

The tumor growth data was analyzed by two methods to determine what dose of 7 would be equivalent to the Taxol® positive control. In the first method only the treatment groups that resulted in tumor regression were considered. The delay in reaching a tumor size of 125 mg was measured from the start of treatment and then normalized against the delay observed for the Taxol® group. The relative delay was plotted against paclitaxel dose equivalents of 7, yielding a data set that showed a linear dose response up to the MTD of 7. The fitted curve indicated that 7 achieved parity with Taxol® at a dose of 1.75 dose equivalents of paclitaxel. In the second analysis the delay in reaching a tumor size of 300 mg was measured relative the saline negative control and then normalized against the delay observed for the Taxol® group. Plotting the relative delay against paclitaxel dose equivalents of 7 again yielded a linear dose response which showed that parity with the Taxol® group was achieved with 1.65 paclitaxel equivalents of 7. Importantly, when the nanoparticle formulation of 7 was dosed at 2 molar paclitaxel equivalents (69 µmol/kg) its MTD (69 µmol/kg), the antitumor activity was significantly greater than that achieved with Taxol® administered at its MTD. Specifically, tumors treated with the nanoparticle formulation of 7 at MTD remained below 50 mg at day 60 in contrast to tumors treated with Taxol® at MTD which had grown to nearly 300 mg (FIG. 4).

FIG. 5 shows the calculation of the number of paclitaxel equivalents of 7 to reach parity with Taxol™.

The effects of dose on the efficacy of 7 nanoparticles was evaluated relative to Taxol®. The optimal therapeutic response was observed with a Q2D dosing in the HT29 solid tumor model. The nanoparticles used to formulate 7 have an elimination half life of approximately 24-36 h, while 7 itself has a partitioning half life of about 10 h. These values are consistent with an effective release of prodrug at the tumor site over a period of approximately two days post-administration, coinciding with the Q2D schedule. Titration of drug dose through 0.25× to 3× paclitaxel equivalents compared to Taxol® at MTD showed that 7 achieved equivalent efficacy at approximately 1.7 paclitaxel equivalents. Since the dose response for 7 is linear up to the MTD it is possible to significantly improve efficacy over the maximum tolerated dose of Taxol® using higher doses of 7. Prodrugs which are better retained than 7 in nanoparticles would achieve parity at even lower doses than that seen for 7.

References (1) Hennenfent, K. L.; Govindan, R. Novel formulations of taxanes: a review. Old wine in a new bottle?, *Ann. Oncol.* 2006, 17, 734-749

(2) Hamaguchi, T.; Matsumura, Y.; Suzuki, M.; Shimizu, K.; Goda, R.; Nakamura, I.; Yokoyama, M.; Kataoka, K.; Kakizoe, T. NK105, a paclitaxel-incorporating micellar nanoparticle formulation, can extend in vivo antitumor activity and reduce the neurotoxicity of palitaxel, *Br. J. Cancer* 2005, 92, 1240-1246

(3) Ansell, S. Lipophilic drug derivatives for use in liposomes. U.S. Pat. No. 5,534,499 1996

(4) Hostetler, K. Y.; Sridhar, N.C. Prodrugs for oral administration containing Taxol covalently bound to a phospholipid. U.S. Pat. No. 5,484,809 1996

(5) Stevens, P. J.; Sekido, M.; Lee, R. J. A folate receptor-targeted lipid nanoparticle formulation for a lipophilic paclitaxel prodrug. *Pharm. Res.* 2004, 21, 2153-2157

(6) Perkins, W. R.; Ahmad, I.; Li, X.; Hirsh, D. J.; Masters, G. R.; Fecko, C. J.; Lee, J. K.; Ali, S.; Nguyen, J.; Schupsky, J.; Herbert, C.; Janoff, A. S.; Mayhew, E. Novel therapeutic nano-particles (lipocores): trapping poorly water soluble compounds. *Int. J. Pharm.* 2000, 200, 27-39

(7) Ali, S.; Ahmad, I.; Peters, A.; Masters, G.; Minchey, S.; Janoff, A. S.; Mayhew, E. Hydrolyzable hydrophobic taxanes: synthesis and anti-cancer activities. *Anticancer Drugs* 2001, 12, 117-128

(8) Lundberg, B. B.; Risovic, V.; Ramaswamy, M.; Wasan, K. M. A lipophilic paclitaxel derivative incorporated in a lipid emulsion for parenteral administration. *J. Control. Release* 1003, 86, 93-100

(9) Rodrigues, D. C.; Maria, D. A.; Fernandes, D. C.; Valduga, C. J.; Couto, R. D.; Ibanez, O. C. M.; Maranhao, R. C. Improvement of paclitaxel therapeutic index by derivatization and association to a cholesterol-rich microemulsion: in vitro and in vivo studies. Cancer *Chemother. Pharmacol.* 2005, 55, 565-576

(10) Zakharian, T. Y.; Seryshev, A.; Sitharaman, B.; Gilbert, B. E.; Knight, V.; Wilson, L. J. A fullerene-paclitaxel chemotherapeutic: synthesis, characterization and study of biological activity in tissue culture. *J. Am. Chem. Soc.* 2005, 127, 12508-12509

(11) Bradley, M. O.; Webb, N. L.; Anthony, F. H.; Devanesan, P.; Witman, P. A.; Hemamalini, S.; Chander, M. C.; Baker, S. D.; He, L.; Horwits, S. B.; Swindell, C. S. Tumor targeting by covalent conjugation of a natural fatty acid to paclitaxel. *Clin. Cancer Res.* 2001, 7, 3229-3238

(12) Deutsch, H. M.; Glinski, J. A.; Hernandez, M.; Haugwitz, R. D.; Narayanan, V. L.; Suffness, M.; Zalkow, L. H. Synthesis of congeners and prodrugs. 3. Water-soluble prodrugs of taxol with potent antitumor activity. *J. Med. Chem.* 1989, 32, 788-792

(13) Johnson, B. K.; Prud'homme, R. K. Flash nanoprecipitation of organic actives and block copolymers using a confined impinging jets mixer. *Aust. J. Chem.* 2003, 56, 1021-1024

(14) Johnson, B. K.; Prud'homme, R. K. Mechanism for rapid self-assembly of block copolymer nanoparticles. *Phys. Rev. Lett.* 2003, 91, 118302

(15) Fetterly, G. J.; Straubinger, R. M. Pharmacokinetics of paclitaxel-containing liposomes in rats, *AAPS PharmSci* 2003, 5, 1-11

(16) Sparreboom, A.; Scripture, C. D.; Trieu, V.; Williams, P. J.; De, T; Yang, A.; Beals, B.; Figg, M. Hawkins, W. D.; Desai, N. Comparative preclinical and clinical pharmacokinetics of a cremophor free, nanoparticle albumin-bound paclitaxel (ABI-007) and paclitaxel formulated in cremophor (Taxol). *Clin. Cancer Res.* 2005, 11, 4136-4143

(17) Sparreboom, A.; van Zuylen, L.; Brouwer, E.; Loos, W. J.; de Bruijn, P.; Gelderblom, H.; Pillay, M; Nooter, K.; Stoter, G.; Verweij, J. Cremophor EL-mediated alteration of paclitaxel distribution in human blood: Clinical pharmacokinetic implications. *Cancer Res.* 1999, 59, 1454-1457

The invention claimed is:

1. A pharmaceutical taxane composition which comprises nanoparticles or micelles wherein said micelles or nanoparticles are formed from noncovalently associating a conjugate of a taxane covalently coupled to a hydrophobic molecule through a diglycolate linker with a lipid and/or an amphiphilic stabilizer.

2. The composition of claim 1 wherein said conjugate is associated with a lipid and an amphiphilic stabilizer.

3. The composition of claim 2 wherein the lipid is a phospholipid and the amphiphilic stabilizer is a copolymer.

4. The composition of claim 3 wherein said copolymer is a copolymer of polyethylene glycol and polystyrene.

5. The composition of claim 4 which further contains an additional antineoplastic agent formulated to mimic the pharmacokinetics of the taxane composition.

6. A method to administer a taxane to a subject which method comprises administering to said subject the composition of claim 2.

7. The method of claim 6 which further comprises administering an additional antineoplastic agent formulated to mimic the pharmacokinetics of the taxane composition.

8. The composition of claim 1 wherein the taxane is paclitaxel or docetaxel.

9. The composition of claim 1 wherein the hydrophobic moiety is a long-chain alcohol, a tocopherol, or a steroid.

10. The composition of claim 1 wherein the lipid is a phospholipid or a tocopherol.

11. The composition of claim 1 wherein the amphiphilic stabilizer is a copolymer.

12. The composition of claim 11 wherein said copolymer is a copolymer of polyethylene glycol and polystyrene.

13. The composition of claim 1 which further contains an additional antineoplastic agent formulated to mimic the pharmacokinetics of the taxane composition.

14. A method to administer a taxane to a subject which method comprises administering to said subject the composition of claim 1.

15. The method of claim 14 which further comprises administering an additional antineoplastic agent formulated to mimic the pharmacokinetics of the taxane composition.

16. A method to prepare the composition of claim 1 which method comprises rapidly mixing water and a miscible solvent containing said conjugate, lipid, and/or amphiphilic stabilizer in a confined space using controlled flow rates.

* * * * *

UNITED STATES PATENT AND TRADEMARK OFFICE
CERTIFICATE OF CORRECTION

PATENT NO. : 8,486,924 B2
APPLICATION NO. : 12/741954
DATED : July 16, 2013
INVENTOR(S) : Ansell et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 379 days.

Signed and Sealed this
Eighth Day of September, 2015

Michelle K. Lee
*Director of the United States Patent and Trademark Office*